United States Patent
Flohr et al.

(10) Patent No.: US 11,109,823 B2
(45) Date of Patent: Sep. 7, 2021

(54) METHOD FOR CONTROLLING A X-RAY IMAGING DEVICE, X-RAY IMAGING DEVICE, COMPUTER PROGRAM AND ELECTRONICALLY READABLE STORAGE MEDIUM

(71) Applicant: Siemens Healthcare GmbH, Erlangen (DE)

(72) Inventors: Thomas Flohr, Uehlfeld (DE); Bernhard Schmidt, Fuerth (DE); Katharine Lynn Rowley Grant, Rochester, MN (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 265 days.

(21) Appl. No.: 16/191,687

(22) Filed: Nov. 15, 2018

(65) Prior Publication Data
US 2019/0150864 A1 May 23, 2019

(30) Foreign Application Priority Data
Nov. 21, 2017 (EP) .................................... 17202756

(51) Int. Cl.
*A61B 6/03* (2006.01)
*G06T 11/00* (2006.01)
(Continued)

(52) U.S. Cl.
CPC ............ *A61B 6/4241* (2013.01); *A61B 6/032* (2013.01); *A61B 6/482* (2013.01); *A61B 6/504* (2013.01);
(Continued)

(58) Field of Classification Search
CPC ....... A61B 6/4241; A61B 6/032; A61B 6/482; A61B 6/504; A61B 6/5294; A61B 6/544;
(Continued)

(56) References Cited

U.S. PATENT DOCUMENTS

| | | | | |
|---|---|---|---|---|
| 2007/0076842 A1* | 4/2007 | Tkaczyk | ............... | A61B 6/4085 378/5 |
| 2014/0023181 A1* | 1/2014 | Noshi | .................. | A61B 6/4241 378/98 |
| 2015/0281564 A1 | 10/2015 | Shin | | |

OTHER PUBLICATIONS

Huda et al., Technique Factors and Image Quality as Functions of Patient Weight at Abdominal CT, Nov. 2000, Radiology, vol. 217, No. 2, pp. 430-435 (Year: 2000).*
(Continued)

*Primary Examiner* — David P Porta
*Assistant Examiner* — Jeremy S Valentiner
(74) *Attorney, Agent, or Firm* — Harness, Dickey & Pierce, P.L.C.

(57) ABSTRACT

A method is for controlling an x-ray imaging device, in particular a computed tomography device. The x-ray imaging device includes an x-ray source and a photon counting detector as an x-ray detector. The methods includes, for an image acquisition process of a patient: determining at least one input parameter relating to at least one of an attenuation property of the patient and a purpose of the image acquisition; at least one of determining or adapting at least one operation parameter of the x-ray detector, dependent upon the at least one input parameter determined; and performing the image acquisition using the at least one operation parameter determined or adapted.

26 Claims, 2 Drawing Sheets

(51) Int. Cl.
*G06T 5/00* (2006.01)
*G06T 7/00* (2017.01)
*A61B 6/00* (2006.01)

(52) U.S. Cl.
CPC ............ *A61B 6/5294* (2013.01); *A61B 6/544* (2013.01); *G06T 5/002* (2013.01); *G06T 7/0012* (2013.01); *G06T 11/008* (2013.01); *A61B 6/405* (2013.01); *A61B 6/4042* (2013.01); *A61B 6/463* (2013.01); *A61B 6/466* (2013.01); *A61B 6/481* (2013.01); *A61B 6/488* (2013.01); *G06T 2207/10116* (2013.01)

(58) Field of Classification Search
CPC ....... A61B 6/4042; A61B 6/405; A61B 6/463; A61B 6/466; A61B 6/481; A61B 6/488
See application file for complete search history.

(56) References Cited

OTHER PUBLICATIONS

European Search Report for European Patent Application No. 17202756.7 dated Jun. 7, 2018.

\* cited by examiner

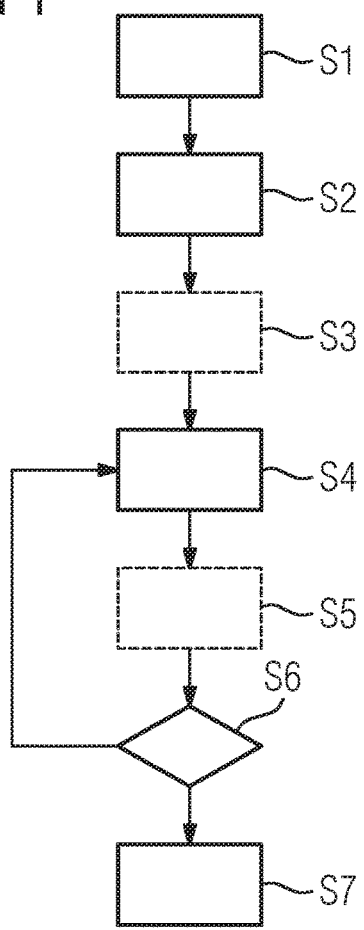
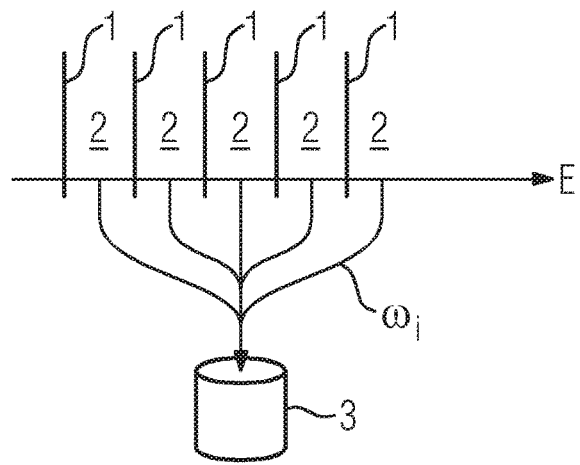

METHOD FOR CONTROLLING A X-RAY IMAGING DEVICE, X-RAY IMAGING DEVICE, COMPUTER PROGRAM AND ELECTRONICALLY READABLE STORAGE MEDIUM

PRIORITY STATEMENT

The present application hereby claims priority under 35 U.S.C. § 119 to European patent application number EP17202756.7 filed Nov. 21, 2017, the entire contents of which are hereby incorporated herein by reference.

FIELD

Embodiments of the invention generally concern a method for controlling an x-ray imaging device such as a computed tomography device, the x-ray imaging device comprising an x-ray source and a photon counting detector as an x-ray detector. Embodiments of the invention further generally concern an x-ray imaging device such as a computer tomography device, a computer program and an electronically readable storage medium.

BACKGROUND

Photon counting detectors (also called single-photon detectors) are known in the state of the art and have also been proposed for x-ray imaging, in particular as pixel detectors. In every pixel, the number of converted x-ray photons is counted, in particular in at least one energy bin (energy interval), which may be defined by at least one energy threshold. It has also been proposed to count photons for multiple, for example two, four or more, energy bins defined by respective thresholds. Photon counting detectors able to count photons in different energy bins are particularly suited for multi energy x-ray imaging, for example dual energy computed tomography (CT), since a broad spectrum may be used at the x-ray source and the spectral separation is performed by defining respective energy bins in the photon counting detector as x-ray detector.

Typically, a tube voltage for the x-ray source of 120 or 140 kV is used to achieve optimised spectral separation. However, if, for example, a computer tomography angiography (CTA) using a contrast agent is to be performed, the goal is to achieve an optimised separation regarding the iodine signal of the contrast agent while material characterisation/separation is of less interest. If the above-mentioned voltages are used at the x-ray source, a loss in iodine contrast due to these high peak kilovoltages (kVp) occurs, so that lower voltages have to be used at least for contrast enhanced scans.

Established technical methods to acquire clinical spectral CT data, i.e. to perform dual energy CT, comprise kVp switching, dual layer CT using two x-ray detectors and dual source dual energy CT. For user-selected source peak voltage or source peak voltage combinations, the acquired x-ray data may be reconstructed using a fixed mixing ratio of high and low kV data. A similar procedure is performed in the case of x-ray imaging devices equipped with at least one photon counting detector as x-ray detector. X-ray data from different thresholds or energy bins are combined using a fixed metric.

Optimisation regarding the image quality of the resulting images is performed manually, in particular after the scan, such that, for example, multiple images may be reconstructed from the x-ray data in different combinations, such that the user may select images of optimal quality.

Regarding operation parameters of the x-ray source, it has been proposed to automatically assist an operator of the x-ray imaging device by automatically choosing, for example, the source current and/or the source peak voltage of the x-ray source depending on certain input parameters. The goal in this case is mainly to reduce patient dose. For example, adjusting the source current to the patient's size and shape may allow dose savings up to 68%.

In a system proposed by the applicant, such as a support tool regarding tube voltage adjustment, also the source peak voltage can be optimised to reduce patient dose, in particular minimising patient dose while maintaining a specified image quality. In particular, a constant contrast to noise ratio (CNR) can be used as a boundary condition. The lowering of the source peak voltage (kVp) typically leads to an increase in contrast and thus potentially allows more noise and therefore less dose while image quality is kept constant. Such a tool may therefore automatically recommend the optimal source peak voltage and source current depending on certain input parameters, in particular comprising input parameters describing an attenuation property of the patient, for example size and/or shape, and/or input parameters describing a purpose of the image acquisition, for example using a slider defining required contrast properties. Such a slider may define the objective of an imaging process, for example if no contrast agent is to be used, bone or internal organs are to be diagnosed and/or a contrast-enhanced imaging is to be performed.

SUMMARY

At least embodiment of the invention to provides a supporting tool for operators of x-ray imaging devices, in particular computer tomography devices, allowing, in particular, a more efficient use of photon counting detectors.

Embodiments of the invention provide a method, an x-ray imaging device, a computer program and an electronically readable storage medium. Advantageous embodiments are described by the claims.

At least one embodiment is directed to a method for controlling an x-ray imaging device, wherein the x-ray imaging device comprises an x-ray source and a photon counting detector as an x-ray detector, comprises the following for each image acquisition process of a patient:

at least one input parameter describing an attenuation property of the patient and/or a purpose of the image acquisition is determined, at least one operation parameter of the x-ray detector is determined and/or adapted dependent on the at least one input parameter, and image acquisition is performed using the determined at least one operation parameter of the x-ray detector.

At least one embodiment is directed to a method method for performing image acquisition of a patient using an x-ray imaging device including an x-ray source and an x-ray detector, comprising: determining at least one input parameter relating to at least one of an attenuation property of the patient and a purpose of the image acquisition;

at least one of determining or adapting at least one operation parameter of the x-ray detector, dependent upon the at least one input parameter determined; and performing the image acquisition using the at least one operation parameter determined.

An x-ray imaging device according to an embodiment of the invention comprises an x-ray source, a photon counting detector as an x-ray detector, and a control device adapted to perform a method according to an embodiment of the invention. All remarks relating to an embodiment of the inventive method may also be applied to the inventive x-ray imaging device.

An X-ray imaging device according to an embodiment of the invention comprises:
an x-ray source;
a photon counting detector; and
a controller, adapted to
   determine at least one input parameter relating to at least one of an attenuation property of the patient and a purpose of the image acquisition,
   at least one of determine or adapt at least one operation parameter of the photon counting detector, dependent upon the at least one input parameter determined, and
   perform the image acquisition using the at least one operation parameter determined or adapted.

The x-ray imaging device may preferably be a computer tomography device (CT device). The control device may comprise a processor and/or a memory to perform the method according to an embodiment of the invention. In a concrete embodiment, the control device may comprise an input parameter determining unit for determining the at least one input parameter, an operation parameter determining unit for determining the at least one operation parameter of the x-ray detector, and an acquisition unit for controlling the acquisition of x-ray data according to the at least one operation parameter. In particular, the operation parameter determining unit may also determine operation parameters for the x-ray source in corresponding embodiments.

A computer program according to an embodiment of the invention can be directly loaded into a memory of a control device of an x-ray imaging device and comprises program segments to perform the steps of a method described herein if the computer program is executed in the control device of the x-ray imaging device. The computer program may be stored on an electronically readable storage medium according to an embodiment of the invention, which comprises electronically readable control information stored thereon and comprising at least one computer program according to an embodiment of the invention. The control information is adapted such that a method according to an embodiment of the invention is performed when the electronically readable storage medium is used in a control device of an x-ray imaging device. Preferably, the electronically readable storage medium is non-transitory, for example a CD-ROM.

A non-transitory electronically readable storage medium, according to an embodiment of the invention, stores a computer program, the computer program including program segments for performing the method of an embodiment of the invention, when the computer program is executed by a processor.

BRIEF DESCRIPTION OF THE DRAWINGS

Further advantages and details of the current invention can be seen from the following description of example embodiments taken in conjunction with the drawings, in which:

FIG. 1 is a flow chart of an embodiment of the method according to the invention, FIG. 2 illustrates the combination of x-ray data of different energy bins into a pseudo-monoenergetic image.

DETAILED DESCRIPTION OF THE EXAMPLE EMBODIMENTS

Figure 3:
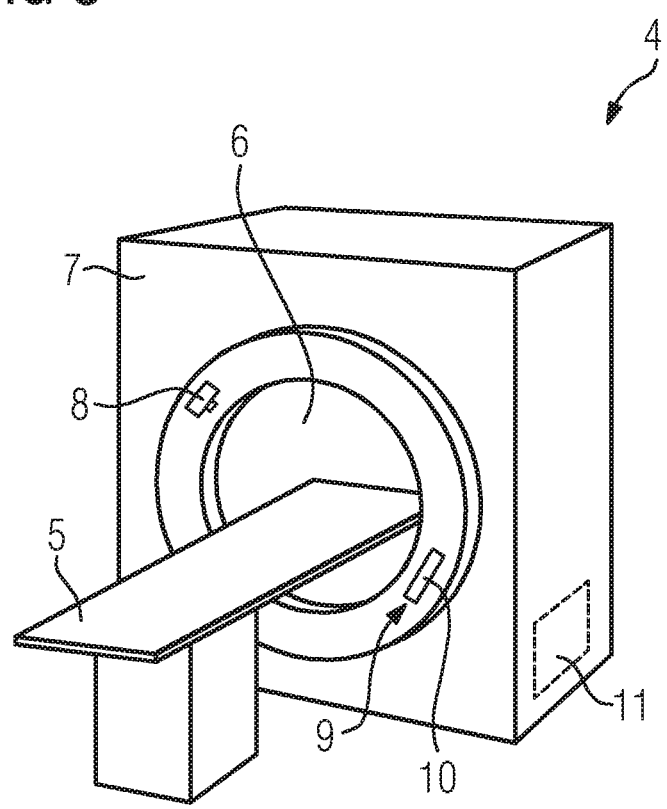
FIG. 3 is a principle drawing of an x-ray imaging device according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a method for controlling an x-ray imaging device, wherein the x-ray imaging device comprises an x-ray source and a photon counting detector as an x-ray detector, comprises the following for each image acquisition process of a patient:
- at least one input parameter describing an attenuation property of the patient and/or a purpose of the image acquisition is determined,
- at least one operation parameter of the x-ray detector is determined and/or adapted dependent on the at least one input parameter, and
- image acquisition is performed using the determined at least one operation parameter of the x-ray detector.

It is thus proposed to use a clinical task-specific input regarding the patient and/or the goal of the image acquisition, i.e. describing which information is to be included in a resulting image, to optimise operation parameters of the photon counting detector, preferably in addition to operation parameters of the x-ray source, which require at least partly the same input parameters.

To this end, the at least one input parameter may comprise at least one of a dimension of the patient and/or a weight of the patient and/or an age of the patient and/or the type of image to be acquired and/or the type of image acquisition and/or desired contrast information, in particular comprising information on a used contrast agent, and/or a reference acquisition parameter suitable for a reference patient. In particular, input parameters also used for tools such as a support tool regarding tube voltage adjustment may also be used for determining at least one operation parameter of the x-ray detector, designed as a photon counting detector.

Desired image quality and/or image properties may be defined regarding a reference patient and/or the type of image to be acquired and/or of image acquisition process to be performed. A reference patient may for example be defined as a patient of a reference weight and/or a reference age or gender, for whom example images with corresponding operation parameters of the x-ray source are available or imaginable, such that, for example, reference acquisition parameters describing operation parameters of the x-ray source to acquire an image containing a required information from the reference patient can be input by a user. Alternatively or additionally, a slider with predetermined positions assigned to respective clinic tasks may be used to acquire at least one input parameter.

Additionally and/or alternatively to deriving the input parameters from such at least one user input, the at least one input parameter may also be derived from results of a pre-scan of the patient and/or information derived from a patient information database, for example from a hospital information system, a radiology information system and/or an electronic patient record (EPR or EHR—electronic health record). It is noted that such patient information may also already comprise information on the clinical task to be performed, in particular the type of image to be acquired and/or the type of image acquisition and/or desired contrast information, in particular describing which materials are to be contrasted to be able to derive diagnostic information during reading of the resultant image. In other words, at least one input parameter describing clinical indication-based requirements and/or the clinical task can be derived from different sources.

Preferably, the operation parameter comprises a number of energy bins and/or the width of energy bins and/or the location of energy bins, in particular described by photon energy thresholds, and/or weighing parameters of energy bins in image reconstruction. The at least one input parameter may thus be used to select optimised threshold values defining energy bins, defining which photons are to be counted in the x-ray detector. That is, optimal energy threshold levels and also the number energy thresholds in the x-ray detector can be selected and adjusted automatically. Moreover, the thresholds could be adapted dynamically to the attenuation of the patient or based on the regions imaged/clinical tasks being accomplished.

Additionally, in particular in the case of pseudo-monoenergetic images to be acquired, also weighing parameters of energy bins in image reconstruction can be adjusted/chosen automatically. That is, by appropriately mixing the x-ray data (i.e., counts) from each of the energy bins, a single image data set is created automatically at the scanner, taking into account the knowledge of the clinical task and/or patient properties.

An embodiment of the invention now allows the optimisation of the mixing ratio of spectral x-ray data and/or the selection of the energy level of pseudo-monoenergetic images based on the at least one input parameters. For example, user-selected input parameters, for example a slider setting "CTA", can be used to select an optimal mixing ratio, i.e. weighing parameters, for spectral x-ray data to obtain pseudo-monoenergetic images showing the best iodine contrast to noise ratio for reading, in the example of "CTA". However, if the at least one input parameter, in particular slider setting, indicates a non-contrast image acquisition process, the respective optimisation of the weighing parameters of spectral x-ray data from the bins or a selection of a monoenergetic energy level may result in different weighing parameters/monoenergetic energy level, in particular to obtain the lowest image noise/best contrast to noise ratio and thus provide an optimal prerequisite for best task-dependent image quality.

Preferably, the energy thresholds/energy bins are optimised as well as the weighing parameters to achieve optimal image quality dependent on the clinical task to be performed and/or on patient properties. It is noted that the mixing of spectral x-ray data from the different energy bins defined by the energy thresholds may, in some cases, already take place in the x-ray detector itself, such that it outputs one single image, simplifying the whole image reconstruction process. However, the combination of spectral x-ray data from different energy bins may also be performed in an image reconstruction unit of the x-ray imaging device. Furthermore, also reconstruction parameters, in particular weighing parameters, regarding different multi energy imaging applications, for example known from dual layer CT, dual source CT and/or kVp switching, may also be optimised based on the at least one input parameter. It is noted that, while in these imaging techniques multiple images had to be reconstructed and subsequently combined, using the photon counting detector allows immediate reconstruction of the required images by accordingly mixing spectral x-ray data from the different energy bins.

In a concrete embodiment, energy bins located at lower energies and/or smaller energy bin widths are used at lower irradiated diameters of the patient and/or for a desired higher contrast, in particular using a contrast agent. In the latter case, it is also preferred to rate energy bins, that is, the respective spectral x-ray data, at lower energies higher than energy bins at higher energies when mixing into an image. If an iodine contrast agent is used, an important energy value is the 33 keV K-edge of iodine. This can be taken into account when optimising the operation parameters of the x-ray source regarding contrast. It is also possible, to, for example, use a narrower energy bin at lower energies. This may result in increased noise, which may, however, be compensated or even be overcompensated by improvement regarding the contrast. In general, for shorter irradiated lengths of patients, that is, thinner patients, less noise is to be expected such that narrower energy bins may be chosen.

To determine optimal operation parameters of the x-ray detector, it is conceivable to empirically create a look up table associating input parameter values with corresponding optimal operation parameters of the x-ray device. Since this, however, requires a large effort and not necessarily meets any possible combinations of input parameters and operation parameters, at least one embodiment of the invention proposes preferred alternative approaches.

In an advantageous embodiment, the at least one operation parameter is at least partly derived from the at least one input parameter in an optimisation process, in which an image quality measure, in particular the contrast to noise ratio, is maximised. Optimisation algorithms as known in the state of the art may be applied. Preferably, the image quality measure, in particular the contrast to noise ratio, is calculated from the at least one input parameter and at least one candidate parameter for the at least one operation parameter using a theoretical model and/or a model trained by machine learning. While image quality measures, in particular the contrast to noise ratio, can, in principle, be calculated in a theoretical framework, it is also possible to train a model using artificial intelligence algorithms by machine learning. Such a model allows to evaluate candidate parameters, since the resulting image quality measure may be included into a cost function of the optimisation process. There may be additional optimisation goals, as will be further described below.

In another preferred embodiment of the invention, the at least one operation parameter is at least partly derived from the at least one input parameter by using an artificial intelligence algorithm trained using training data including a ground truth provided by at least one reviewing expert. While less preferred than explicit optimisation regarding the resulting image quality, the determination process of the operation parameters of the x-ray detector may also be realised by using an artificial intelligence algorithm which maps input parameters to operation parameters of the x-ray detector. Known artificial intelligence techniques of the state of the art may be employed in this embodiment.

In an especially preferred embodiment, as also mentioned above, at least one, in particular all, of the at least one input parameter is also used for determining at least one operation parameter of the x-ray source, in particular the source peak voltage and/or the source current. As initially described, support tools for operators regarding the operation parameters of the x-ray source (x-ray tube) are already known in the state of the art and provide an advantageous foundation for the current invention. In particular, at least one embodiment of the current invention can be added to an already provided functionality of automatically determining, for example, a source peak voltage (kVp, in particular tube peak voltage) and/or source current (tube current). This fusion of support tools for an operator of the x-ray imaging device has the advantage that essentially the same input parameters can be used. Thus, based on, for example, user input regarding the optimisation of source operation parameters, also operation parameters of the x-ray detector can be selected and adjusted automatically, in particular optimal energy thresholds and/or energy bins and/or reconstruction parameters relating to the properties of photon counting detectors.

Preferably, at least one operation parameter of the x-ray source is determined in an optimisation process minimising the radiation dose applied to the patient. The concrete fusion of two operator supporting functionalities, namely automatically choosing and/or adjusting operation parameters of the x-ray source as well as the x-ray detector, may be achieved in numerous ways.

In a possible embodiment, the operation parameters for both the x-ray detector and the x-ray source are determined in a shared optimisation process, in particular minimising radiation dose as well as contrast to noise ratio. However, in this combined optimisation approach, two optimisation goals at least partly opposing each other are pursued, wherein one of them, namely reduction of patient dose, may have to be rated stronger. It is thus preferred to perform determination of the operation parameters of the x-ray source and determination of the operation parameters of the x-ray detector into subsequent steps, allowing higher flexibility and task-related improvement of a determination of the respective operation parameters. Even in such an embodiment, preferably, the known properties of the photon counting detector are taken into account when determining the operation parameters of the x-ray source, since many photon counting detectors provide better results at higher peak energies and thus higher peak voltages of an x-ray tube of the x-ray source. In an embodiment, the optimisation process for the operation parameters of the x-ray source takes into account at least one property of the x-ray detector, in particular the photon counting detector requiring higher energies for higher image quality.

In an especially advantageous embodiment, as discussed above, in a first step, the at least one operation parameter of the x-ray source is determined depending on at least one of the at least one input parameter and, in a subsequent second step, the at least one operation parameter of the x-ray detector is determined dependent on the at least one input parameter and at least one of the at least one operation parameter of the x-ray source, in particular in an optimisation process maximising an image quality measure, preferably the contrast to noise ratio. Thus, preferably, a two-step-optimisation is performed, wherein in a first step, a global optimisation process minimising patient dose may be performed regarding the operation parameters of the x-ray source, optionally taking into account properties of the photon counting detector, while in a second step, the operation parameters of the x-ray source, in particular peak voltages, are accepted as a given and an additional optimisation process maximising image quality is performed.

In this manner, both the requirements of low patient dose and high image quality may be achieved. This may, as noted, comprise compromising regarding the operation parameters of the x-ray source. For example if a low peak voltage of 80 kV may be optimal for patient dose. However, since it is known that a photon counting detector is used, this may be adjusted to 100 kV, still being lower than an initially proposed value of the corresponding operation parameter.

The automatic determination and/or adjustment of operation parameters, in particular for the x-ray detector, may be performed automatically or semi-automatically. In the latter case, it may be provided that the determined operation parameters for the x-ray detector are output to a user and applied upon confirmation and/or modification by the user. In this variant of at least one embodiment of the inventive method, the determined operation parameters for the x-ray detector are output to a user for confirmation or possible adjustment by the user, so that the determined operation parameters can be seen as a proposal or a recommendation.

Preferably, at least one of the at least one operation parameter of the x-ray detector is dynamically updated during the image acquisition process, in particular dependent on information on the patient area currently imaged and/or the current imaging geometry and/or state information regarding the time phase in functional imaging. A dynamic adaptation could therefore be realised in the space domain, for example along the patient's length axis, but also over time, for example in the case of dynamic computer tomography angiography (CTA) and/or perfusion scans.

For example, if multiple fields of view of the patient are scanned subsequently, for example by moving the acquisition arrangement from the head to the shoulder of the patient, different distances through the patient and/or different materials in the patient have to be traversed by the x-ray radiation, resulting in a different attenuation during the same acquisition process, which can be determined from an acquisition protocol and/or using a dedicated sensor and/or the x-ray detector itself. Additionally or alternatively, the evolution of an image process, for example perfusion and/or dynamic CTA, can be tracked in time, providing information on contrast and/or attenuation changing over time. This may also lead to adjustments of the operation parameters to maintain a high image quality or even improve the image quality. Thus, dynamic adaptation during x-ray data acquisition is advantageous both in the space domain and in the time domain.

In another preferred embodiment, if a monoenergetic image is to be reconstructed, the energy level of the monoenergetic image is chosen dependent on at least one of the at least one input parameter, and/or if at least one multi energy image is to be reconstructed, at least one reconstruction parameter used in reconstruction is chosen dependent on at least one of the at least one input parameter. While the energy level of the pseudo-monoenergetic image could still be interpreted as an operation parameter of the x-ray detector, in particular if the image is reconstructed in the x-ray detector itself, at least one embodiment of the invention also allows for determination and/or adjustment of reconstruction parameters and/or further image processing parameters, further improving a quality of the resultant images taking into account the properties of the photon counting detector. Reconstruction parameters may, for example, be applied for reconstructing images showing a certain material and/or predetermined attenuation properties, as is in principle known from multi energy x-ray imaging, in particular dual energy CT.

It should additionally be noted that in particular input parameters relating to the patient to be imaged can also be derived from sensor data of sensors associated with the x-ray imaging device. For example, it has been proposed to use cameras and/or other sensors to determine the position and/or dimensions of the patient.

An x-ray imaging device according to an embodiment of the invention comprises an x-ray source, a photon counting detector as an x-ray detector, and a control device adapted to perform a method according to an embodiment of the invention. Al remarks relating to an embodiment of the inventive method may also be applied to the inventive x-ray imaging device. The x-ray imaging device may preferably be a computer tomography device (CT device). The control device may comprise a processor and/or a memory to perform the method according to an embodiment of the invention. In a concrete embodiment, the control device may comprise an input parameter determining unit for determining the at least one input parameter, an operation parameter determining unit for determining the at least one operation parameter of the x-ray detector, and an acquisition unit for controlling the acquisition of x-ray data according to the at least one operation parameter. In particular, the operation parameter determining unit may also determine operation parameters for the x-ray source in corresponding embodiments.

A computer program according to an embodiment of the invention can be directly loaded into a memory of a control device of an x-ray imaging device and comprises program segments to perform the steps of a method described herein if the computer program is executed in the control device of the x-ray imaging device. The computer program may be stored on an electronically readable storage medium according to an embodiment of the invention, which comprises electronically readable control information stored thereon and comprising at least one computer program according to an embodiment of the invention. The control information is adapted such that a method according to an embodiment of the invention is performed when the electronically readable storage medium is used in a control device of an x-ray imaging device. Preferably, the electronically readable storage medium is non-transitory, for example a CD-ROM.

In the following, a preferred embodiment of the invention will be described for the example of a computer tomography device (CT device) as x-ray imaging device.

According to a step S1 in the flow chart of FIG. 1, input parameters describing an attenuation property of a patient to be imaged and/or a purpose of the image acquisition are determined. In this embodiment, the size, at least the height, of the patient, a weight of the patient and an age of the patient are used as patient-related input parameters.

Further input parameters, in this case, describe the clinical task underlying the image acquisition process and define the type of image to be acquired, desired contrast properties, the type of image acquisition (in particular contrast enhanced imaging or non-contrast enhanced imaging) and acquisition parameters referring to a reference patient. These input parameters may be, at least in part, automatically determined, for example from sensor data of at least one sensor scanning the patient, a patient information data base, in particular an electronic patient record, and/or evaluation results of a pre-scan of the patient.

While, in this embodiment, the patient-related input parameters are indeed automatically derived, input parameters describing the clinical task are derived from user input, in particular at a user interface of an input device of the x-ray imaging device. In this case, a user interface known from the support tool e.g. regarding optimized individual dose or tube voltage adjustment is used.

Acquisition parameters referring to a reference patient define a reference quality, in this case using a reference source current and a reference peak voltage. For example, these reference values can be set for a standard patient of 75 kg as reference patient. However, these input parameters are optional since possible initial values for an optimisation process may also be derived from the clinical task information provided by the user via, for example, a slider. Such a slider may indicate the type of image acquisition being performed, in particular sorted regarding the desired contrast properties. For example, a slider on the far right side may indicate a vascular examination, while moving the slider to the left will optimise settings for less iodine content until, at the far left, a non-contrast scan is indicated.

Once the input parameters have been determined in step S1, in a step S2, using a two-substep procedure, operation parameters for the x-ray source and the x-ray detector, which is a photon counting detector, are determined by respective optimisation processes. In a first substep, an optimisation process is performed regarding the source current and the source peak voltage (tube current and tube peak voltage) as operation parameters for the x-ray source, minimising the patient dose, as known in the state of the art. However, in possible embodiments, properties of the photon counting detector may be included into the optimisation process for the operation parameters of the x-ray source, for example as boundary conditions and/or additional terms of the cost function. In a concrete embodiment, higher energies and thus higher source peak voltages may be favoured to provide good spectral separation in the photon counting detector.

In a second substep of step S2, a second optimisation process is performed, this time regarding the operation parameters of the x-ray detector, that is, the photon counting detector. As an input, additionally to the input parameters the operation parameters of the x-ray source are used. The operation parameters of the x-ray detector in this embodiment define energy bins, i.e. comprise certain energy thresholds. Additionally, weighing parameters for reconstructing a pseudo-monoenergetic image from the spectral x-ray data of the individual energy bins are determined, wherein this pseudo-monoenergetic image may already be reconstructed in the x-ray detector itself. The operation parameters of the x-ray detector are determined maximising an image quality measure, in this case the contrast to noise ratio, which can be calculated using a mathematical model. This model may be a theoretical model or an artificial intelligence model trained using machine learning.

FIG. 2 illustrates the operation parameters of the x-ray detector used in this embodiment. Energy thresholds 1 define energy bins 2, that is, energy intervals, for which photons are separately counted, yielding spectral x-ray data. These spectral x-ray data for the individual energy bins 2 may be mixed using weighing factors ωi to obtain a pseudo-monoenergetic image 3. For example, in computer tomography angiography (CTA), the number, position and width of the energy bins 2 as well as the weighing factors ωi may be chosen to yield the best contrast to noise ratio regarding the separation of iodine materials from other materials.

It is noted that, in other embodiments, it is also possible to use a combined optimisation process for both the operation parameters of the x-ray source of the operation parameters of the x-ray detector.

In an optional step S3, cf. FIG. 1, the determined operation parameters may be output to a user, who may confirm these operation parameters for use or modify them, resulting in a semi-automatic determination.

In a step S4, image acquisition commences using the determined (and optionally confirmed or modified) operation parameters for the x-ray source and the x-ray detector.

An optional step S5 denotes dynamic adaptation of the operation parameters, wherein dynamic adaption may be performed in the space domain, in particular along the length of the patient, and/or in the time domain, in particular when imaging dynamic processes like perfusion. Input parameters relevant for updating the operation parameters of the x-ray detector (and optionally also the x-ray source) may be derived from an acquisition protocol used, sensor data of an attenuation sensor and/or x-ray data of the x-ray detector.

In a step S6, it is checked if all x-ray data has been acquired. If not, the image acquisition process is continued in step S4. Alternatively, in a step S7, the at least one reconstructed acquired image can be output and/or further processed. It is noted that, in a preferred embodiment, in particular when performing multi energy x-ray imaging, in particular dual energy CT, reconstruction parameters leading to an optimal image quality may also be derived automatically from the input parameters and/or operation parameters, taking into account the properties of the photon counting detector.

FIG. 3 is a principle drawing of an embodiment of an inventive x-ray imaging device 4, in this case a CT-device. The x-ray imaging device 4 comprises a patient table 5 which may be moved into the opening 6 of a gantry 7 in which the x-ray source 8 and the x-ray detector 9, which is a photon counting detector 10, can be rotated around a patient on the patient table 5. A control device 11 of the x-ray imaging device 4 is adapted to perform the method described with respect to FIGS. 1 and 2. In this respect, the x-ray imaging device 4 may also comprise a display device and/or input device (not shown). The control device 11 may be connected to information systems, for example a patient information data base and the like.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing image acquisition of a patient using an x-ray imaging device including an x-ray source and an x-ray detector, the method comprising:
   determining at least one input parameter relating to at least one of an attenuation property of the patient or a purpose of the image acquisition;
   determining at least one operation parameter of the x-ray detector using an algorithm for increased image quality, the algorithm based on the at least one input parameter;

calculating a contrast to noise ratio from the at least one input parameter and at least one candidate parameter for the operation parameter using a model trained by machine learning; and
performing the image acquisition using the at least one operation parameter.

2. The method of claim 1, wherein the at least one input parameter includes at least one of:
a dimension of the patient;
a weight of the patient;
an age of the patient;
a type of image to be acquired;
a type of image acquisition;
desired contrast information; or
an acquisition parameter referring to a reference patient.

3. The method of claim 2, further comprising:
deriving the at least one input parameter from at least one of
a user input,
evaluation results of a pre-scan of the patient, or
information derived from a patient information database.

4. The method of claim 3, wherein the at least one operation parameter comprises at least one of:
a number of energy bins;
a width of the energy bins; or
a location of the energy bins in image reconstruction.

5. The method of claim 2, wherein the at least one operation parameter comprises at least one of:
a number of energy bins;
a width of the energy bins; or
a location of the energy bins in image reconstruction.

6. The method of claim 2, further comprising:
determining at least one operation parameter of the x-ray source based on at least one of the at least one input parameter.

7. The method of claim 1, wherein the at least one operation parameter comprises at least one of:
a number of energy bins;
a width of the energy bins; or
a location of the energy bins in image reconstruction.

8. The method of claim 7, wherein the location of the energy bins is described by at least one of photon energy thresholds and weighing parameters of the energy bins.

9. The method of claim 1, further comprising:
determining at least one operation parameter of the x-ray source based on at least one of the at least one input parameter.

10. The method of claim 9, further comprising:
determining the at least one operation parameter of the x-ray source in a process to decrease a radiation dose applied to the patient.

11. The method of claim 10, wherein the method further comprises:
determining the operation parameters for the x-ray detector and the x-ray source in a shared process.

12. The method of claim 11, wherein the method further comprises:
determining the operation parameters for the x-ray detector and the x-ray source in a shared process for reducing radiation dose and contrast to noise ratio.

13. The method of claim 10, wherein,
the determining the at least one operation parameter of the x-ray source includes determining the at least one operation parameter of the x-ray source based on at least one of the at least one input parameter; and
the determining the at least one operation parameter of the x-ray detector includes determining the at least one operation parameter of the x-ray detector based on the at least one input parameter and at least one of the at least one operation parameter of the x-ray source.

14. The method of claim 10, wherein the process for reducing the radiation dose and contrast to noise ratio is based on at least one property of the x-ray detector.

15. The method of claim 14, wherein the process for reducing the radiation dose and contrast to noise ratio is based on at least one property of a photon counting detector requiring relatively higher energies for relatively higher image quality.

16. The method of claim 9, further comprising:
determining at least one of a source peak voltage and a source current based on at least one of the at least one input parameter.

17. The method of claim 1, wherein the determined at least one operation parameter of the x-ray detector includes a plurality of operation parameters, the method further comprising:
outputting the plurality of operation parameters for the x-ray detector to a user; and
applying the plurality of operation parameters in response to at least one of confirmation or modification by the user.

18. The method of claim 1, further comprising:
dynamically updating at least one of the at least one operation parameter of the x-ray detector during the performing the image acquisition.

19. The method of claim 18, wherein the image acquisition is dependent on at least one of information on an area of the patient currently imaged, current imaging geometry, and state information regarding time phase in functional imaging.

20. The method of claim 1, further comprising:
selecting an energy level of a monoenergetic image based on at least one of the at least one input parameter, in response to the monoenergetic image being reconstructed.

21. The method of claim 20, further comprising:
selecting at least one reconstruction parameter used in reconstruction based on at least one of the at least one input parameter, in response to at least one multi energy image being reconstructed.

22. A non-transitory computer device storing a computer program, adapted to perform the method of the claim 1 when the computer program is executed by a controller of an x-ray imaging device.

23. A non-transitory electronically readable storage medium storing a computer program, the computer program including program segments for performing the method of the claim 1 when the computer program is executed by a processor.

24. The method of claim 1, further comprising:
deriving the at least one input parameter from at least one of
a user input,
evaluation results of a pre-scan of the patient, or
information derived from a patient information database.

25. The method of claim 1, further comprising
selecting at least one reconstruction parameter used in reconstruction based on at least one of the at least one input parameter, in response to at least one multi energy image being reconstructed.

26. An x-ray imaging device, comprising:
an x-ray source;
a photon counting detector; and
a controller configured to cause the x-ray imaging device to,
- determine at least one input parameter relating to at least one of an attenuation property of a patient or a purpose of image acquisition,
- determine at least one operation parameter of the photon counting detector using an algorithm for increased image quality, the algorithm based on the at least one input parameter,
- calculate a contrast to noise ratio from the at least one input parameter and at least one candidate parameter for the operation parameter using a model trained by machine learning, and
- perform the image acquisition using the at least one operation parameter determined or adapted.

\* \* \* \* \*